(12) United States Patent
Pohl et al.

(10) Patent No.: US 7,045,334 B2
(45) Date of Patent: May 16, 2006

(54) NUCLEOTIDE SEQUENCE ENCODING A BENZALDEHYDE LYASE, AND PROCESS FOR STEREOSELECTIVELY SYNTHESIZING 2-HYDROXYKETONES

(75) Inventors: Martina Pohl, Aachen (DE); Michael Müller, Jülich (DE); Ayhan Demir, Ankara (TR)

(73) Assignee: Forschungszentrum Jülich GmbH, Jülich (DE)

( * ) Notice: Subject to any disclaimer, the term of this patent is extended or adjusted under 35 U.S.C. 154(b) by 293 days.

(21) Appl. No.: 10/336,048

(22) Filed: Jan. 2, 2003

(65) Prior Publication Data

US 2004/0014182 A1    Jan. 22, 2004

Related U.S. Application Data

(63) Continuation-in-part of application No. PCT/EP01/07426, filed on Jun. 29, 2001.

(30) Foreign Application Priority Data

Jul. 3, 2000    (DE) ................ 100 32 254

(51) Int. Cl.
*C12N 9/88* (2006.01)
*C12N 15/00* (2006.01)
*C12P 21/06* (2006.01)
*C07K 1/00* (2006.01)
*C07H 21/04* (2006.01)

(52) U.S. Cl. .............. 435/232; 435/69.1; 435/320.1; 435/325; 435/252.3; 530/350; 536/23.2

(58) Field of Classification Search ................ 435/232, 435/69.1, 320.1, 325, 252.3; 530/350; 536/23.2
See application file for complete search history.

(56) References Cited

FOREIGN PATENT DOCUMENTS

WO    WO 99 09195 A    *    2/1999

OTHER PUBLICATIONS

Witkowski et al. , Biochemistry 38:11643-11650, 1999.*
Seffernick et al. , J. Bacteriol. 183(8):2405-2410, 2001.*
Hinrichsen Patricio et al: "Cloning and sequencing of the gene encoding benzaldehyde lyase from *Pseudonomas fluorescens biovar I*", GENE (Amsterdam) vol. 144 No. 1, 1994 pp. 137-138.*
Iding et al: Benzylformate decarboxylase from Pseudomonas putida as stable catalyst for the synthesis of chiral 2-hydroxy ketones, Chemistry—a European Journal., vol. 6 No. 8, Apr. 14, 2000, pp. 1483-1495.*
Gonzales B et al: Benzaldehyde Lyase a novel Thiamine PP-I-Requiring enzyme from Pseudomonas-Fluorescens Biavar I, Journal of Bacteriology, vol. 171, No. 5, 1989, pp. 2401-2405.*

* cited by examiner

*Primary Examiner*—Rebecca E. Prouty
*Assistant Examiner*—Delia M. Ramirez
(74) *Attorney, Agent, or Firm*—Klaus J. Bach

(57) ABSTRACT

The present invention relates to a nucleotide sequence which encodes a benzaldehyde lyase and to its use in a process for stereoselectively preparing 2-hydroxyketone group-containing compounds.

3 Claims, No Drawings

SEQUENCE LISTING

```
<160> NUMBER OF SEQ ID NOS: 2

<210> SEQ ID NO 1
<211> LENGTH: 1689
<212> TYPE: DNA
<213> ORGANISM: Pseudomonas fluorescens
<220> FEATURE:
<221> NAME/KEY: CDS
<222> LOCATION: (1)..(1689)
<223> OTHER INFORMATION: Benzaldehyd-Lyase

<400> SEQUENCE: 1 atg gcg atg att aca ggc ggc gaa ctg gtt gtt cgc acc cta ata aag        48
Met Ala Met Ile Thr Gly Gly Glu Leu Val Val Arg Thr Leu Ile Lys
 1               5                  10                  15 gct ggg gtc gaa cat ctg ttc ggc ctg cac ggc gcg cat atc gat acg        96
Ala Gly Val Glu His Leu Phe Gly Leu His Gly Ala His Ile Asp Thr
             20                  25                  30 att ttt caa gcc tgt ctc gat cat gat gtg ccg atc atc gac acc cgc       144
Ile Phe Gln Ala Cys Leu Asp His Asp Val Pro Ile Ile Asp Thr Arg
         35                  40                  45 cat gag gcc gcc gca ggg cat gcg gcc gag ggc tat gcc cgc gct ggc       192
His Glu Ala Ala Ala Gly His Ala Ala Glu Gly Tyr Ala Arg Ala Gly
     50                  55                  60 gcc aag ctg ggc gtg gcg ctg gtc acg gcg ggg gga ttt acc aat           240
Ala Lys Leu Gly Val Ala Leu Val Thr Ala Gly Gly Gly Phe Thr Asn
 65                  70                  75                  80 gcg gtc acg ccc att gcc aac gct tgg ctg gat cgc acg ccg gtg ctc       288
Ala Val Thr Pro Ile Ala Asn Ala Trp Leu Asp Arg Thr Pro Val Leu
                 85                  90                  95
```

| | | |
|---|---|---|
| ttc ctc acc gga tcg ggc gcg ctg cgt gat gat gaa acc aac acg ttg<br>Phe Leu Thr Gly Ser Gly Ala Leu Arg Asp Asp Glu Thr Asn Thr Leu<br>100 105 110 | | 336 |
| cag gcg ggg att gat cag gtc gcc atg gcg gcg ccc att acc aaa tgg<br>Gln Ala Gly Ile Asp Gln Val Ala Met Ala Ala Pro Ile Thr Lys Trp<br>115 120 125 | | 384 |
| gcg cat cgg gtg atg gca acc gag cat atc cca cgg ctg gtg atg cag<br>Ala His Arg Val Met Ala Thr Glu His Ile Pro Arg Leu Val Met Gln<br>130 135 140 | | 432 |
| gcg atc cgc gcc gcg ttg agc gcg cca cgc ggg ccg gtg ttg ctg gat<br>Ala Ile Arg Ala Ala Leu Ser Ala Pro Arg Gly Pro Val Leu Leu Asp<br>145 150 155 160 | | 480 |
| ctg ccg tgg gat att ctg atg aac cag att gat gag gat agc gtc att<br>Leu Pro Trp Asp Ile Leu Met Asn Gln Ile Asp Glu Asp Ser Val Ile<br>165 170 175 | | 528 |
| atc ccc gat ctg gtc ttg tcc gcg cat ggg gcc aga ccc gac cct gcc<br>Ile Pro Asp Leu Val Leu Ser Ala His Gly Ala Arg Pro Asp Pro Ala<br>180 185 190 | | 576 |
| gat ctg gat cag gct ctc gcg ctt ttg cgc aag gcg gag cgg ccg gtc<br>Asp Leu Asp Gln Ala Leu Ala Leu Leu Arg Lys Ala Glu Arg Pro Val<br>195 200 205 | | 624 |
| atc gtg ctc ggc tca gaa gcc tcg cgg aca gcg cgc aag acg gcg ctt<br>Ile Val Leu Gly Ser Glu Ala Ser Arg Thr Ala Arg Lys Thr Ala Leu<br>210 215 220 | | 672 |
| agc gcc ttc gtg gcg gcg act ggc gtg ccg gtg ttt gcc gat tat gaa<br>Ser Ala Phe Val Ala Ala Thr Gly Val Pro Val Phe Ala Asp Tyr Glu<br>225 230 235 240 | | 720 |
| ggg cta agc atg ctc tcg ggg ctg ccc gat gct atg cgg ggc ggg ctg<br>Gly Leu Ser Met Leu Ser Gly Leu Pro Asp Ala Met Arg Gly Gly Leu<br>245 250 255 | | 768 |
| gtg caa aac ctc tat tct ttt gcc aaa gcc gat gcc gcg cca gat ctc<br>Val Gln Asn Leu Tyr Ser Phe Ala Lys Ala Asp Ala Ala Pro Asp Leu<br>260 265 270 | | 816 |
| gtg ctg atg ctg ggg gcg cgc ttt ggc ctt aac acc ggg cat gga tct<br>Val Leu Met Leu Gly Ala Arg Phe Gly Leu Asn Thr Gly His Gly Ser<br>275 280 285 | | 864 |
| ggg cag ttg atc ccc cat agc gcg cag gtc att cag gtc gac cct gat<br>Gly Gln Leu Ile Pro His Ser Ala Gln Val Ile Gln Val Asp Pro Asp<br>290 295 300 | | 912 |
| gcc tgc gag ctg gga cgc ctg cag ggc atc gct ctg ggc att gtg gcc<br>Ala Cys Glu Leu Gly Arg Leu Gln Gly Ile Ala Leu Gly Ile Val Ala<br>305 310 315 320 | | 960 |
| gat gtg ggt ggg acc atc gag gct ttg gcg cag gcc acc gcg caa gat<br>Asp Val Gly Gly Thr Ile Glu Ala Leu Ala Gln Ala Thr Ala Gln Asp<br>325 330 335 | | 1008 |
| gcg gct tgg ccg gat cgc ggc gac tgg tgc gcc aaa gtg acg gat ctg<br>Ala Ala Trp Pro Asp Arg Gly Asp Trp Cys Ala Lys Val Thr Asp Leu<br>340 345 350 | | 1056 |
| gcg caa gag cgc tat gcc agc atc gct gcg aaa tcg agc agc gag cat<br>Ala Gln Glu Arg Tyr Ala Ser Ile Ala Ala Lys Ser Ser Ser Glu His<br>355 360 365 | | 1104 |
| gcg ctc cac ccc ttt cac gcc tcg cag gtc att gcc aaa cac gtc gat<br>Ala Leu His Pro Phe His Ala Ser Gln Val Ile Ala Lys His Val Asp<br>370 375 380 | | 1152 |
| gca ggg gtg acg gtg gta gcg gat ggt gcg ctg acc tat ctc tgg ctg<br>Ala Gly Val Thr Val Val Ala Asp Gly Ala Leu Thr Tyr Leu Trp Leu<br>385 390 395 400 | | 1200 |
| tcc gaa gtg atg agc cgc gtg aaa ccc ggc ggt ttt ctc tgc cac ggc<br>Ser Glu Val Met Ser Arg Val Lys Pro Gly Gly Phe Leu Cys His Gly | | 1248 |

-continued

```
                 405                 410                 415
tat cta ggc tcg atg ggc gtg ggc ttc ggc acg gcg ctg ggc gcg caa         1296
Tyr Leu Gly Ser Met Gly Val Gly Phe Gly Thr Ala Leu Gly Ala Gln
                420                 425                 430 gtg gcc gat ctt gaa gca ggc cgc cgc acg atc ctt gtg acc ggc gat         1344
Val Ala Asp Leu Glu Ala Gly Arg Arg Thr Ile Leu Val Thr Gly Asp
            435                 440                 445 ggc tcg gtg ggc tat agc atc ggt gaa ttt gat acg ctg gtg cgc aaa         1392
Gly Ser Val Gly Tyr Ser Ile Gly Glu Phe Asp Thr Leu Val Arg Lys
        450                 455                 460 caa ttg ccg ctg atc gtc atc atg aac aac caa agc tgg ggg gcg             1440
Gln Leu Pro Leu Ile Val Ile Ile Met Asn Asn Gln Ser Trp Gly Ala
465                 470                 475                 480 aca ttg cat ttc cag caa ttg gcc gtc ggc ccc aat cgc gtg acg ggc         1488
Thr Leu His Phe Gln Gln Leu Ala Val Gly Pro Asn Arg Val Thr Gly
                485                 490                 495 acc cgt ttg gaa aat ggc tcc tat cac ggg gtg gcc gcc gcc ttt ggc         1536
Thr Arg Leu Glu Asn Gly Ser Tyr His Gly Val Ala Ala Ala Phe Gly
            500                 505                 510 gcg gat ggc tat cat gtc gac agt gtg gag agc ttt tct gcg gct ctg         1584
Ala Asp Gly Tyr His Val Asp Ser Val Glu Ser Phe Ser Ala Ala Leu
        515                 520                 525 gcc caa gcg ctc gcc cat aat cgc ccc gcc tgc atc aat gtc gcg gtc         1632
Ala Gln Ala Leu Ala His Asn Arg Pro Ala Cys Ile Asn Val Ala Val
    530                 535                 540 gcg ctc gat ccg atc ccg ccc gaa gaa ctc att ctg atc ggc atg gac         1680
Ala Leu Asp Pro Ile Pro Pro Glu Glu Leu Ile Leu Ile Gly Met Asp
545                 550                 555                 560 ccc ttc taa                                                              1689
Pro Phe
```

<210> SEQ ID NO 2
<211> LENGTH: 562
<212> TYPE: PRT
<213> ORGANISM: Pseudomonas fluorescens

<400> SEQUENCE: 2

```
Met Ala Met Ile Thr Gly Gly Glu Leu Val Val Arg Thr Leu Ile Lys
1               5                   10                  15

Ala Gly Val Glu His Leu Phe Gly Leu His Gly Ala His Ile Asp Thr
            20                  25                  30

Ile Phe Gln Ala Cys Leu Asp His Asp Val Pro Ile Ile Asp Thr Arg
        35                  40                  45

His Glu Ala Ala Gly His Ala Ala Glu Gly Tyr Ala Arg Ala Gly
    50                  55                  60

Ala Lys Leu Gly Val Ala Leu Val Thr Ala Gly Gly Phe Thr Asn
65              70                  75                  80

Ala Val Thr Pro Ile Ala Asn Ala Trp Leu Asp Arg Thr Pro Val Leu
                85                  90                  95

Phe Leu Thr Gly Ser Gly Ala Leu Arg Asp Asp Glu Thr Asn Thr Leu
            100                 105                 110

Gln Ala Gly Ile Asp Gln Val Ala Met Ala Ala Pro Ile Thr Lys Trp
        115                 120                 125

Ala His Arg Val Met Ala Thr Glu His Ile Pro Arg Leu Val Met Gln
    130                 135                 140

Ala Ile Arg Ala Ala Leu Ser Ala Pro Arg Gly Pro Val Leu Leu Asp
145                 150                 155                 160
```

-continued

| | | | | | | | | | | | | | | |
|---|---|---|---|---|---|---|---|---|---|---|---|---|---|---|
|Leu|Pro|Trp|Asp|Ile|Leu|Met|Asn|Gln|Ile|Asp|Glu|Asp|Ser|Val|Ile|
| | | |165| | | |170| | | |175| | | |

Ile Pro Asp Leu Val Leu Ser Ala His Gly Ala Arg Pro Asp Pro Ala
        180             185             190

Asp Leu Asp Gln Ala Leu Ala Leu Leu Arg Lys Ala Glu Arg Pro Val
        195             200             205

Ile Val Leu Gly Ser Glu Ala Ser Arg Thr Ala Arg Lys Thr Ala Leu
        210             215             220

Ser Ala Phe Val Ala Ala Thr Gly Val Pro Val Phe Ala Asp Tyr Glu
225             230             235             240

Gly Leu Ser Met Leu Ser Gly Leu Pro Asp Ala Met Arg Gly Gly Leu
            245             250             255

Val Gln Asn Leu Tyr Ser Phe Ala Lys Ala Asp Ala Ala Pro Asp Leu
            260             265             270

Val Leu Met Leu Gly Ala Arg Phe Gly Leu Asn Thr Gly His Gly Ser
            275             280             285

Gly Gln Leu Ile Pro His Ser Ala Gln Val Ile Gln Val Asp Pro Asp
        290             295             300

Ala Cys Glu Leu Gly Arg Leu Gln Gly Ile Ala Leu Gly Ile Val Ala
305             310             315             320

Asp Val Gly Gly Thr Ile Glu Ala Leu Ala Gln Ala Thr Ala Gln Asp
            325             330             335

Ala Ala Trp Pro Asp Arg Gly Asp Trp Cys Ala Lys Val Thr Asp Leu
            340             345             350

Ala Gln Glu Arg Tyr Ala Ser Ile Ala Ala Lys Ser Ser Glu His
        355             360             365

Ala Leu His Pro Phe His Ala Ser Gln Val Ile Ala Lys His Val Asp
        370             375             380

Ala Gly Val Thr Val Val Ala Asp Gly Ala Leu Thr Tyr Leu Trp Leu
385             390             395             400

Ser Glu Val Met Ser Arg Val Lys Pro Gly Gly Phe Leu Cys His Gly
            405             410             415

Tyr Leu Gly Ser Met Gly Val Gly Phe Gly Thr Ala Leu Gly Ala Gln
            420             425             430

Val Ala Asp Leu Glu Ala Gly Arg Arg Thr Ile Leu Val Thr Gly Asp
            435             440             445

Gly Ser Val Gly Tyr Ser Ile Gly Glu Phe Asp Thr Leu Val Arg Lys
450             455             460

Gln Leu Pro Leu Ile Val Ile Ile Met Asn Asn Gln Ser Trp Gly Ala
465             470             475             480

Thr Leu His Phe Gln Gln Leu Ala Val Gly Pro Asn Arg Val Thr Gly
            485             490             495

Thr Arg Leu Glu Asn Gly Ser Tyr His Gly Val Ala Ala Phe Gly
            500             505             510

Ala Asp Gly Tyr His Val Asp Ser Val Glu Ser Phe Ser Ala Ala Leu
            515             520             525

Ala Gln Ala Leu Ala His Asn Arg Pro Ala Cys Ile Asn Val Ala Val
            530             535             540

Ala Leu Asp Pro Ile Pro Pro Glu Glu Leu Ile Leu Ile Gly Met Asp
545             550             555             560

Pro Phe

NUCLEOTIDE SEQUENCE ENCODING A BENZALDEHYDE LYASE, AND PROCESS FOR STEREOSELECTIVELY SYNTHESIZING 2-HYDROXYKETONES

This application is a continuation in part of application PCT/EP01/07426 filed on Jun. 29, 2001.

BACKGROUND OF THE INVENTION

The present invention relates to an improved process for stereoselectively synthesizing 2-hydroxyketones using a benzaldehyde lyase.

A thiamine pyrophosphate (TPP)-dependent benzaldehyde lyase, and genetic analyses of the encoding gene, are described in Vicuna et al. (J. Bacteriol., 1989, 171: 2401–2405) and Hinrichsen, P. et al. (Gene, 1994, 144: 137–138). More detailed characterization of the enzyme showed that this benzaldehyde lyase only possesses an irreversible cleaving activity. Thus, for example, two molecules of benzaldehyde are formed when benzoin is used as the starting compound, while anisoin is cleaved into two molecules of anisaldehyde. The possibility of a benzaldehyde lyase catalyzing any linking of C—C compounds is explicitly ruled out.

Decarboxylases or transketolases, which are as a rule likewise dependent on thiamine pyrophosphate (TPP), are particularly suitable for the enzyme-catalyzed synthesis of 2-hydroxyketones.

Whitesides et al. (J. Org. Chem., 1992, 57:5889–5907) and Turner et al. (Tetrahedron Asymmetry, 1996, 7: 2185–2188) describe transketolases which catalyze the cleavage of a 2-hydroxyketone with the simultaneous formation of another 2-hydroxyketone. However, these references do not de-scribe any economic production processes for preparing 2-hydroxyketones using transketolases.

The enzymic synthesis of 2-hydoxyketones in the presence of a TPP-dependent pyruvate decarboxylase has also been described (DE 195 23 269 and DE 297 36 104). However, a disadvantage of the methods which are described is that the pyruvate decarboxylase only accepts a highly restricted substrate spectrum. In addition, the resulting products can spontaneously racemize due to the occurrence of keto-enol tautomerism, resulting in a decrease in the enantioselectivity.

Wilcocks et al. (Biotech. Bioeng., 1992, 39: 1058–1063 and Appl. Env. Microbiol., 1992, 58: 1699–1704) describe using a thiamine pyrophosphate-dependent benzoyl formate decarboxylase to synthesize (S)-2-hydroxy-1-phenylpropanone ((S)-2-HPP) starting from benzoyl formate and acetaldehyde. However, the 2-hydroxyketone which is formed in this case is not enantiomerically pure, either, but is only formed in an enantiomeric excess of 92%. Another disadvantage is that benzyl alcohol is formed as a byproduct when whole cells are used.

The object of the present invention is therefore to make available an improved enzymic process for preparing 2-hydroxyketones, which process no longer suffers from the previously mentioned disadvantages.

SUMMARY OF THE INVENTION

This object is achieved by the process according to the invention for stereoselectively preparing 2-hydroxy-ketones, employing a benzaldehyde lyase which, in the presence of at least one solubility-promoting compound, catalyzes the reaction of two aldehyde group-containing compounds, at least one of which is not an acetaldehyde, or catalizes from an aldehyde group-containing compound with a 2-hydroxy-ketone group-containing compound, while retaining the stereochemical alignment of the latter, to another 2-hydroxyketone group-containing compound.

In one embodiment of the present invention, the previously mentioned process is characterized by the fact that a first aldehyde group-containing compound of the formula I

-- where R is= a component from the group of aliphatic, aromatic or heteroaromatic hydrocarbons which can be substituted once or more than once in the ortho, meta or para position, where the substituents can be alkyl, aryl or aralkyl groups or heteroatoms such as Cl, F, Br or S, P, N or combinations thereof, and R is ≠ —$CH_3$ --, is converted with a second compound of the formula I to form a 2-hydroxyketone group-containing compound of the formula II,

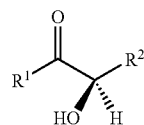

where $R^1$ and $R^2$ can be identical or different and $R^1$ and $R^2$ have the same meaning as R in formula I.

A selection of examples of compounds of the formula I, and consequently of substrates of the benzaldehyde lyase which are used in accordance with the invention, are listed below:

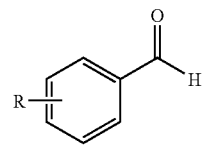

R=2-F, 4-F, 2,4-F, 2-Br, 4-Br, 2-Cl, 4-Cl, 2-$OCH_3$, 3-$OCH_3$, 4-$OCH_3$, 2-OH, 2-$CH_3$

In a preferred embodiment of the process according to the invention, benzaldehyde is used as a compound of the formula I. (R)-Benzoin is a preferred compound of the formula II.

In another embodiment of the present invention, it is possible to synthesize cyclic compounds. For example, steroidal hydroxyketones can, for example, be formed, in accordance with the invention, by intramolecular transpositions of two aldehyde groups. The following formula, where $R^1$ and $R^2$ have the same meaning as in formula II and/or formula I, can be used to further clarify these cyclic compounds.

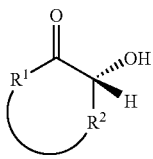

While the following formula serves as an example of a preferred compound, it is only being used for clarification and does not have a limiting effect on the invention.

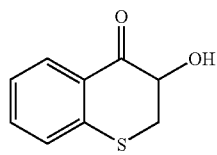

In addition, the present invention encompasses a process in which compounds of the formula II are further reacted, in the presence of aldehyde group-containing compounds of the formula III

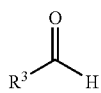

-- where $R^3$ is =—$CH_3$ or a component from the group of aliphatic, aromatic or heteroaromatic hydrocarbons which can be substituted once or more than once in the ortho, meta or para position, where the substituents can be alkyl, aryl or aralkyl groups or heteroatoms such as Cl, F, Br or S, P, N or combinations thereof --, to form compounds of the formula IV

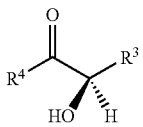

where $R^3 \neq R^4$ and $R^3=R^3$ of the formula III and $R^4=R$ of the formula I.

In a preferred embodiment of the present process, acetaldehyde is used as a compound of the formula III. (R)-2-Hydroxy-1-phenylpropanone ((R)-2-HPP) is a preferred compound of the formula IV.

In a particularly preferred embodiment of the present invention, the process according to the invention represents a combination of the two previously mentioned embodiments, with two aldehyde group-containing compounds reacting, in a first stage, to give a 2-hydroxyketone group-containing compound and, as soon as the latter is present, these 2-hydroxyketones also undergoing a further reaction to give another 2-hydroxyketone group-containing compound. A summary of the course of the reaction is depicted diagrammatically as follows:

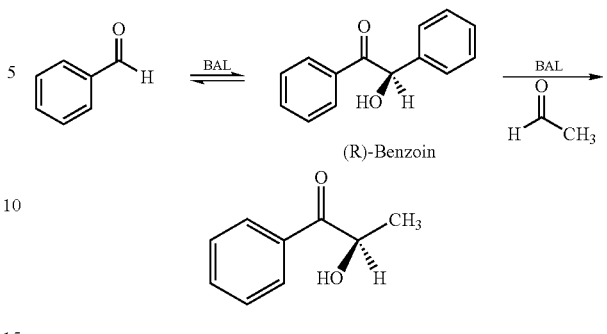

In addition, the present invention also encompasses a process in which, starting with a racemic mixture containing compounds of the formula II, the enantiomer of the formula II is selectively further reacted, while retaining the stereochemical alignment, to give a compound of the formula IV. For clarification, this embodiment is depicted diagrammatically as follows:

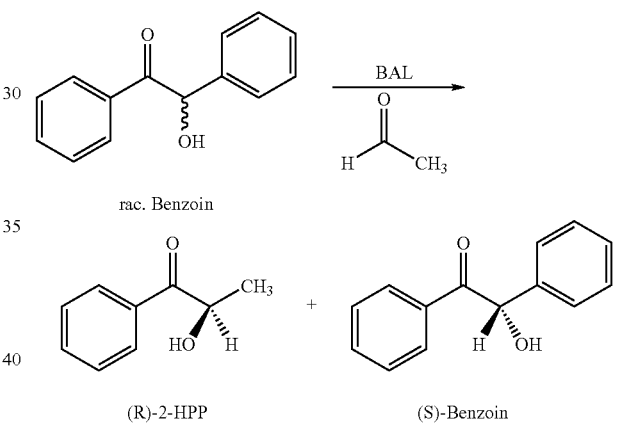

In this diagram, the alignment of the OH group on the α-C atom in relation to the keto group as a wavy line is intended to indicate the presence of a racemic mixture of a 2-hydroxyketone group-containing compound of the formula II. In this connection, the mixture can, for example, be a racemic mixture of (S)- and (R)-benzoin.

The present invention is consequently advantageously characterized by the fact that one and the same catalyst can be used both to prepare (R)-2-hydroxyketones in a highly efficient and enantioselective manner and, when a racemic mixture of 2-hydroxyketone group-containing compounds, for example of the formula II, is present, to separate the two enantiomers in a highly efficient manner. For example, the process according to the invention can be used, on the one hand, to prepare (R)-benzoin virtually quantitatively from benzaldehyde and, on the other hand, to obtain (S)-benzoin and (R)-2-HPP with a comparably high degree of efficiency from a racemic mixture of (S)- and (R)-benzoin. Owing to the different solubility behavior of the two previously mentioned 2-hydroxyketone group-containing enantiomers, i.e. (S)-benzoin and (R)-2-HPP, it is possible to quantitatively separate the (S)- and (R)-forms of the originally employed racemic mixture.

Another embodiment of the process according to the invention is characterized by the fact that an aldehyde group-containing compound of the formula I, as a first substrate, is reacted with an acetaldehyde or substituted acetaldehyde, as a second substrate, by way of a compound of the formula II as intermediate, to give a compound of the formula IV. The following diagrammatic depiction is once again intended to clarify this.

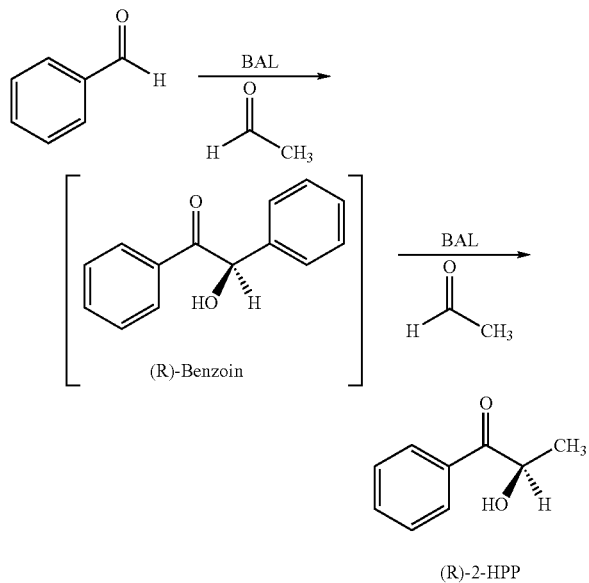

The concept of stereoselectivity or enantioselectivity within the meaning of the present invention is explained more precisely as follows. In a general manner, the process according to the invention makes it possible to prepare 2-hydroxyketone group-containing compounds stereoselectively. Out of the two possible stereoisomers (enantiomers) of the 2-hydroxyketones formed, i.e. out of the (S)- or (R)-enantiomer, it is, according to the invention, exclusively the (R)-enantiomer which is formed, i.e. with an enantioselectivity of virtually 100%, as a result of the benzaldehyde lyase which is used. This (R)-enatiomer which has been formed can then, in a further step of the process according to the invention, function as another substrate of the benzaldehyde lyase and be reacted to give another (R)-2-hydroxyketone group-containing compound.

In this connection, an (R)-enantiomer is to be understood, according to the invention, as meaning a compound in which the OH group on the α-C atom in relation to the keto group protrudes out of the plane of the paper whereas the carbon atoms of the carbonyl backbone and the radicals $R^1$ and $R^2$ (in formula II) and, respectively, $R^3$ and $R^4$ (in formula IV) lie in the plane of the paper. In this connection, this definition according to the invention of an (R)-enantiomer is made without considering the priority of the radicals $R^1/R^2$ and/or respectively $R^3/R^4$ but, on the contrary, exclusively in dependence on the positioning of the hydroxyl group on the α-C atom in relation to the keto group. Consequently, it is possible that the (R) configuration according to the invention is not identical to the customary nomenclature of the stereoisomeric compounds.

What has been said above is explained below taking as an example a compound of the formula II:

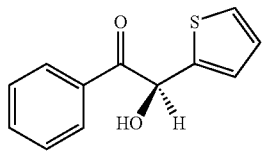

According to the customary nomenclature, this compound is the compound (S)-2-hydroxy-1-phenyl-2-thiophen-2-yletha-none. However, according to the invention, this compound is the (R)-enantiomer since the OH group projects from the plane of the paper while the two carbon atoms of the ketone group, and the radicals $R^1$ and $R^2$, lie in the plane of the paper.

According to the invention, the expression "retaining the stereochemical alignment" is to be understood as meaning that the configuration of the OH group on the α-C atom in relation to the keto group emerges unchanged from the enzyme-catalyzed reaction, that is it is retained.

Surprisingly, when a solubility-promoting compound is employed and when aldehyde group-containing compounds of the formula I are used as the starting material, the enzyme-catalyzed process according to the invention proceeds almost quantitatively in the direction of a 2-hydroxyketone group-containing compound of the formula II. That which has been said also applies to the process variant in which the compounds of the formula II which have been synthesized in a first process stage are further reacted to give compounds of the formula IV.

According to the invention, at least 0.5–40%, preferably 5–20%, particularly preferably 7–12% and most preferably 10%, of at least one solubility-promoting compound is added to the reaction mixture or the culture medium in one of the previously mentioned processes according to the invention. In this connection, an organic solvent which is miscible with water and/or water-soluble, and/or a solvent-free compound, can, according to the invention, be added as a solubility-promoting compound. In this regard, dimethyl sulfoxide (DMSO), dimethylformamide or ethanol may be mentioned as being examples of organic solvents which are miscible with water and/or which are water-soluble. Cyclodextrins, for example β-cyclodextrins (cycloheptaamylose), may be mentioned as examples of a solvent-free compound which can be employed in accordance with the invention.

In addition, the process according to the invention is characterized by the fact that there is an enantiomeric excess (ee) of compound of the formula II which is in the region of ≧96%, preferably of ≧97%, particularly preferably of ≧99%, and in particular of 99.9%.

According to the invention, the present process is furthermore characterized by the fact that an enantiomeric excess (ee) of compound of the formula IV of at least from 50 to 60%, preferably of from 60 to 90%, particularly preferably of from 92 to 97%, and most preferably of from 97 to ≧99.9%, is achieved.

The enantiomeric excess (ee) is the measure of the selectivity of a stereospecific preparation method and can be represented by the following formula: ee=the quantity (%S–%R)=(S–R)/(S+R). By this, the quantity is to be understood as being the difference in the percentage yields of the two isomers ((S)-enantiomer and (R)-enantiomer) which are present in the product. If, for example, one isomer is present to the extent of 20% and the other isomer is present to the extent of 80%, this then results in an enantiomeric excess of 60%.

In another embodiment of the present invention, the process according to the invention is characterized by the fact that it is carried out either as what is termed a fed-batch process or else as a continuously conducted reaction. A large number of appliances which are suitable for this purpose are known from the literature. For example, a suitable reaction vessel is a classical stirred tank reactor (fermenter) which is charged with a suitable medium for culturing cells containing a benzaldehyde lyase according to the invention. By continuously supplying aldehyde group-containing compounds of the formula I and, where appropriate, continuously or discontinuously metering in a solubility-promoting compound, the enzymically synthesized, stereospecific product consisting of an (R)-2-hydroxyketone group-containing compound can be continuously produced and conducted out of the fermenter.

In another process variant of the present invention, 2-hydroxyketone group-containing compounds are synthesized in an enzyme membrane reactor, as is described, for example, in Kula et al. (J. Biotechnol., 1981, 23: 2789–2802). According to the invention, it is possible to achieve product yields in the region of 96–100%, preferably of 97%, particularly preferably of 99% and, in particular, of more than 99%.

The present invention furthermore relates to a process which is characterized by the fact that use is made of a benzaldehyde lyase, or a biologically active moiety thereof, which is encoded by a nucleotide sequence as depicted in SEQ ID No. 1 or an allele, homologue or derivative of this nucleotide sequence or a nucleotide sequence which hybridizes with this latter sequence. In this connection, the present invention also encompasses a process in which use is made of a benzaldehyde lyase having an amino acid sequence as depicted in SEQ ID No. 2, or a biologically active moiety thereof, or a modified form, or isoenzymes or mixtures thereof.

According to the invention, alleles are to be understood as meaning nucleotide sequences which are functionally equivalent, i.e. which essentially have the same effect. Functionally equivalent sequences are those sequences which, despite a differing nucleotide sequence, for example as a result of the degeneracy of the genetic code, still possess the desired functions. Functional equivalents consequently include naturally occurring variants of the sequences which are described herein and also artificial nucleotide sequences, for example nucleotide sequences which have been obtained by chemical synthesis and adapted, where appropriate, to the codon usage of the host organism. In addition to this, functionally equivalent sequences include those which exhibit an altered nucleotide sequence which, for example, confers on the enzyme loss of sensitivity, or resistance, toward inhibitors. Functional equivalents (alleles) are also those variants whose function has been weakened or augmented as compared with the starting gene or gene fragment.

An allele is also understood, in particular, as meaning natural or artificial mutations of an originally isolated sequence which continue to exhibit the desired function. Mutations include substitutions, additions, deletions, transpositions or insertions at one or more nucleotide residues. This also includes what are termed sense mutations which, at the protein level, can lead, for example, to the substitution of conserved amino acids but which do not lead to any fundamental change in the activity of the protein and are consequently functionally neutral. This also includes changes in the nucleotide sequence which, at the protein level, affect the N terminus or C terminus of a protein without, however, significantly impairing the function of the protein. These changes can even exert a stabilizing influence on the protein structure. These mutations furthermore include changes which, for example, facilitate subsequent purification of the protein, such as, for example, what is termed a His tag, which consists of several consecutive histidine residues.

In addition, the present invention also includes, for example, those nucleotide sequences which are obtained by modifying the nucleotide sequence, resulting in corresponding derivatives. The aim of such a modification can, for example, be that of further circumscribing the coding sequence which is contained therein or else that of inserting further recognition cleavage sites for restriction enzymes or that of incorporating rare nucleotides.

Artificial DNA sequences also form part of the present invention as long as they, as described above, mediate the desired properties. Such artificial DNA sequences can be determined, for example, by means of backtranslating proteins which have been generated using computer-assisted programs (molecular modeling), or by means of in-vitro selection. Coding DNA sequences which have been obtained by backtranslating a polypeptide sequence in accordance with the codon usage which is specific for the host organism are particularly suitable. A skilled person who is familiar with molecular genetic methods can readily determine the specific codon usage by carrying out computer analyses of other, already known genes of the organism to be transformed.

According to the invention, homologous sequences are to be understood as meaning those sequences which are complementary to the nucleotide sequences according to the invention and/or which hybridize with these sequences. According to the invention, the term hybridizing sequences includes substantially similar nucleotide sequences from the DNA or RNA group which enter into a specific interaction (binding) with the previously mentioned nucleotide sequences under stringent conditions which are known per se. These hybridizing sequences also include short nucleotide sequences having a length of, for example, from 10 to 30, preferably of from 12 to 15, nucleotides. According to the invention, this also includes, inter alia, what are termed primers or probes.

The sequence regions which precede (5' or upstream) and/or follow (3' or downstream) the coding regions (structural genes) are also included according to the invention. This includes, in particular, sequence regions which possess a regulatory function. They may exert an influence on transcription, RNA stability or RNA processing and also on translation. Examples of regulatory sequences are, inter alia, promoters, enhancers, operators, terminators or translation augmentors.

According to the invention, a biologically active moiety of the enzyme according to the invention is to be understood as meaning any polypeptide sequence which possesses the enzyme activity, which is specific and essential to the invention, for linking C—C compounds. The length of a biologically active moiety of a benzaldehyde lyase according to the invention can, for example, vary in the range from 560±10 amino acid residues to 560±250 amino acid residues, preferably from 560±50 to 560±100, and particularly preferably from 560±25 to 560±50 amino acid residues. In this connection, the "basal number" of 560 amino acid residues corresponds, according to the invention, to a polypeptide sequence of a benzaldehyde lyase as depicted in SEQ ID No. 2, which is encoded by a nucleotide sequence as depicted in SEQ ID No. 1. Consequently, the "basal number" of the polypeptide can likewise vary in dependence on the nucleotide sequence which encodes it.

According to the invention, modified forms are to be understood as meaning enzymes in which changes in the sequence, for example at the N terminus and/or C terminus of the polypeptide, or in the region of conserved amino acids, are present without, however, impairing the function of the enzyme. These changes can be performed by substituting one or more amino acids using methods which are known per se.

One particular embodiment of the present invention encompasses variants of the polypeptides according to the invention whose activity and/or specificity has been weakened or augmented, for example by means of amino acid substitution, as compared with the relevant starting protein. The same applies to the stability of the enzymes according to the invention in the cells, which enzymes are, for example, more susceptible or less susceptible to degradation by proteases.

The present invention furthermore relates to polypeptides which have the function of a benzaldehyde lyase and whose amino acid sequence has been altered such that they are desensitized (feedback-desensitized) toward compounds having a regulatory effect, for example end products of the metabolic pathway.

Isoforms are to be understood as meaning enzymes which have the same, or a comparable, substrate specificity and specificity of effect but which have a different primary structure.

According to the invention, an isolated benzaldehyde lyase of the previously described type, or cell extracts or whole cells containing a benzaldehyde lyase, are used in the present process.

According to the invention, an isolated benzaldehyde lyase and/or a cell extract containing a benzaldehyde lyase according to the invention can be employed, for example in an enzyme membrane reactor. In addition to this, other in-vitro systems for stereoselectively preparing, in accordance with the invention, 2-hydroxyketone group-containing compounds are also included.

Customary culturing methods which are operated batch-wise or fed-batch-wise, or continuous fermentations, are to be mentioned, by way of example, at this point, as being suitable systems for using whole cells which contain a benzaldehyde lyase according to the invention.

The process according to the invention is furthermore characterized by the fact that use is made of a benzaldehyde lyase which is derived from microorganisms, preferably of the genus Pseudomonas or Acinetobacter. Preference is given to using a benzaldehyde lyase which is derived from *Pseudomonas fluorescens* and, in particular, from *Pseudomonas fluorescens biovar I*. In this connection, the present invention also encompasses a benzaldehyde lyase which is derived from what are termed production strains. These strains can be obtained either in a natural manner or in an artificial manner. The latter method includes classical mutagenesis methods or, for example, recombinant DNA methods.

The 2-hydroxyketone group-containing compounds (in brief: 2-hydroxyketones) which have been prepared by a process of the above-described nature are also part of the subject matter of the present invention.

The present invention furthermore encompasses a benzaldehyde lyase which is intended for use in a previously mentioned process and which is encoded by a nucleotide sequence as depicted in SEQ ID No. 1, or an allele, homologue or derivative of this nucleotide sequence, or a nucleotide sequence which hybridizes with this latter sequence. This likewise includes a benzaldehyde lyase which has an amino acid sequence as depicted in SEQ ID No. 2, or else a biologically active moiety or a modified form thereof, or isoenzymes or mixtures thereof.

The benzaldehyde lyase according to the invention can be isolated from microorganisms, preferably the genus Pseudomonas or Acinetobacter. Preferably, the benzaldehyde lyase according to the invention is a benzaldehyde lyase which has been isolated from the species *Pseudomonas fluorescens*, particularly preferably from the species *Pseudomonas fluorescens biovar I*. These comments are by way of example; they are, however, in no way limiting for the present invention. In the same way, the present invention encompasses what are termed production strains for isolating an appropriate benzaldehyde lyase. The present invention furthermore relates to a nucleotide sequence which encodes a benzaldehyde lyase isolated from organisms of the previously described nature.

According to the invention, a nucleotide sequence or a nucleic acid fragment is to be understood as meaning a polymer which is composed of RNA or DNA, which can be single-stranded or double-stranded and which can optionally contain natural, chemically synthesized, modified or artificial nucleotides. In this connection, the term DNA polymer also includes genomic DNA and cDNA or mixtures thereof.

The present invention furthermore relates to a gene structure which contains a previously described nucleotide sequence, which encodes a benzaldehyde lyase according to the invention, and also regulatory sequences which are operatively linked to this nucleotide sequence and which control the expression of the coding sequences in the host cell.

An operative linkage is understood as meaning the sequential arrangement of, for example, promoter, coding sequence, terminator and, where appropriate, other regulatory elements such that each of the regulatory elements is able to fulfill its function, as required, when the coding sequence is expressed. These regulatory nucleotide sequences may be of natural origin or may be obtained by chemical synthesis. In principle, any promoter which is able to control the expression of a gene in the relevant host organism is suitable for use as the promoter. In this connection, the promoter can, according to the invention, also be a chemically inducible promoter which can control the expression of the genes, which are subject to it, in the host cell at a given point in time. A promoter which can be induced with IPTG (isopropyl-β-thiogalactoside) may be mentioned here by way of example.

A gene structure is prepared by using customary recombination and cloning techniques, as are described, for example, in T. Maniatis, E. F. Fritsch and J. Sambrook, Molecular Cloning: A Laboratory Manual, Cold Spring Harbor Laboratory, Cold Spring Harbor, N.Y. (1994), to fuse a suitable promoter to at least one nucleotide sequence according to the invention.

Adapters or linkers can be attached to the DNA fragments for the purpose of linking the fragments together.

In addition to this, the present invention relates to a vector which contains a benzaldehyde lyase-encoding nucleotide sequence of the previously described type, regulatory nucleotide sequences which are operatively linked to this nucleotide sequence, and also additional nucleotide sequences for selecting transformed host cells, for replication within the host cell or for integration into the corresponding host cell genome. Furthermore, the vector according to the invention can contain a gene structure of the previously mentioned type.

The present invention furthermore relates to a transformed unicellular or multicellular organism for use in a process of the previously mentioned type, which organism contains a benzaldehyde lyase and/or a nucleotide sequence of the previously mentioned type. Customary recombinant DNA methods are used for transferring nucleic acid sequences into a host cell. Transformation may be mentioned here as being the preferred method, and the transfer of DNA by means of electroporation may be mentioned as being particularly preferred.

According to the invention, this transformed unicellular or multicellular organism is characterized by the fact that it is a microorganism, a yeast or a fungus, or else an animal cell or a plant cell. The organism which is transformed in accordance with the invention preferably belongs to the enterobacteria group. Particularly preferably, the organism is a transformed organism of the species *Escherichia coli*. Furthermore, strains which are termed production strains and which are suitable for preparing the compounds according to the invention are also included in the present invention.

The present invention furthermore relates to the use of the 2-hydroxyketone group-containing compounds according to the invention for preparing compounds which have an antiviral and/or antifungal effect and/or which have the effect of enzyme inhibitors and which can be employed in areas of pharmacy and/or medicine, for example for treating immune diseases (AIDS) or neurodegenerative diseases (epilepsy).

In this connection, the compounds can, for example, be (chiral) precursors or constituents of antibiotics, such as Chloramphenicol. Genaconazoles (Gala D. et al., 1996, Tetrahedron Letters, 37 (5): 611–614 or Leuenberger H. G. W. et al., 1999, Chimia, 53: 536–540) may, for example, be mentioned here as examples of compounds which have an antifungal effect. This enumeration is to be understood as being only for the purpose of clarifying the use of the 2-hydroxyketones which have been prepared in accordance with the invention, with the enumeration in no way, however, having a limiting effect on the present invention.

The present invention is characterized in more detail by means of the following implementation examples, which are not limiting, however.

General Genetic Methods:

The isolation of gemomic DNA and plasmid DNA, and all the techniques for restriction, Klenow treatment and alkaline phosphatase treatment, and, in addition, methods for cloning and sequencing DNA, and also the transformation, culture and selection of host cells, were carried out as described in T. Maniatis, E. F. Fritsch and J. Sambrook (Molecular Cloning: A Laboratory Manual, Cold Spring Harbor Laboratory, Cold Spring Harbor, N.Y. (1994)).

Protein Expression and Purification

The gene encoding the benzaldehyde lyase was isolated from *Pseudomonas fluorescens* using known methods. The benzaldehyde lyase-encoding gene was then cloned into the inducible vector pKK322-2 (Pharmacia Biotech) and provided with six histidine-encoding triplets at its 3' end. The resulting vector, i.e. pkk322-2::BAL-His, was then transformed into the *E.coli* strain SG13009prep4 (Quiagen, Hilden). The transformed cells were propagated at 37° C. in LB medium in the presence of ampicillin (100 mg/ml). Protein expression is induced with 1 mM isopropyl-β-D-thiogalactoside (IPTG) when the optical density of the cells has reached $OD_{600}$=0.7. The cells were harvested by centrifugation after a further 16 h. Depending on the scale of the culture preparation, the cells were disrupted either mechanically using glass beads or else in a ball mill. The resulting crude cell extract was freed from cell debris by centrifugation and subsequent filtration and then loaded onto a nickel chelate chromatography column (preferably: Ni-NTA-agarose; Qiagen, Hilden). The column had previously been equilibrated with 50 mM potassium phosphate buffer, pH 7.0. Non-binding constituents are flushed out by washing with the equilibration buffer. Subsequently, the same buffer, which had now been supplemented with 50 mM imidazole, was used to elute weakly bound proteins. The benzaldehyde lyase, together with its histidine end (BAL-His), is eluted selectively in the presence of 200 mM imidazole. The collected protein fractions were subsequently rebuffered by subjecting them to a gel filtration in 50 mM potassium phosphate buffer, pH 6.5, containing 1 mM $MgSO_4$ and 0.01 mM thiamine pyrophosphate (TPP). The benzaldehyde lyase was finally lyophilized and stored at −20° C.

Synthesis of (R)-Benzoin from Benzaldehyde 318 mg (3 mM) of benzaldehyde are dissolved in a mixture of 20 ml of DMSO and 100 ml of phosphate buffer (50 mM, pH 7.0) containing 2.5 MM $MgSO_4$ and 0.15 mM TPP. The reaction is started by adding 1 mg (20 U) of benzaldehyde lyase and the reaction mixture is incubated at room temperature for 48 hours. A further 1 mg (20 U) of benzaldehyde lyase is then added. The course of the reaction is observed by means of a combination of gas chromatography and ass spectroscopy (GC-MS) or by means of high pressure liquid chromatography (HPLC). A 97% conversion to (R)-benzoin is reached after 62 hours. The reaction mixture is extracted with 250 ml of dichloromethane, after which the organic phase is washed with 25 ml of dist. water and 25 ml of a saturated solution of NaCl and dried over $Na_2SO_4$. The solvent is then removed in vacuo. Recrystallizing the crude product results in 305 mg (96%) of (R)-benzoin (melting point: 134° C.). The value of the enantiomeric excess (ee) is >99%.

$[\alpha]_D^{22}$=−115 (c=1.5, $CH_3COCH_3$). HPLC (Chiralpac AD, isohexane/isopropanol 90:10; 0.75 ml/min, 20° C., 21 bar) rt: 26.95 min.

If only 10 ml, rather than 20 ml, of DMSO are added to the reaction mixture, under comparable conditions, part of the (R)-benzoin product then precipitates out in crystalline form and can be separated by filtration.

Obtaining (S)-Benzoin and (R)-2-HPP from a Racemic Benzoin Mixture 414 mg (2 mM) of a racemic benzoin mixture are dissolved in a mixture of 20 ml of DMSO and 100 ml of phosphate buffer (50 mM, pH 7.0) containing 2.5 mM $MgSO_4$ and 0.15 mM TPP. 88 mg (2 mM) of acetaldehyde are added to this mixture. The reaction is started by adding 1 mg (20 U) of benzaldehyde lyase and the mixture is incubated at room temperature. After 24 hours, a further 1 mg (20 U) of benzaldehyde lyase and a further 176 mg (4 mM) of acetaldehyde are added. The course of the reaction is observed by means of a combination of gas chromatography and mass spectroscopy (GC-MS) or by means of high pressure liquid chromatography (HPLC). This procedure is repeated every 24 hours until the (R)-benzoin which is present has been completely reacted. HPLC analyses show that, after 4 days, it is only the products (S)-benzoin and (R)-2-HPP which are present in the solution. The reaction mixture is extracted with 250 ml of dichloromethane, after which the organic phase is washed with 25 ml of dist. water and 25 ml of a saturated solution of NaCl and dried over $Na_2SO_4$. The solvent is then removed in vacuo. The crude product is purified by column chromatography on silica gel ($CH_2Cl_2$). This results in 279 mg (93%) of (R)-2-HPP, with the enantiomeric excess (ee) being >99% ($[\alpha]_D^{22}$=−123 (c=2, $CHCl_3$)) and 201 mg (95%) of (S)-benzoin, which likewise has a value for the enantiomeric excess of >99% ($[\alpha]_D^{22}$=114 (c=1.5, $CH_3COCH_3$)); (melting point=134° C.).

(R)-2-HPP: $^1$H NMR (300 MHz, $CDCl_3$, 20° C.): δ=1.47 (d, 3H, $^3J(H,H)$=7.0 Hz; $CH_3$), 3.81 (br, 1H; OH), 5.19 (q, 1H, $^3J(H,H)$=7.0 Hz; CHOH), 7.52 ('t', 2H, $^3J(H,H)$=7.5 Hz; ar-H), 7.64 (tt, 1H, $^3J(H,H)$=7.5 Hz, $^4J(H,H)$=1.3 Hz; ar-H), 7.95 (dd, 2H, $^3J(H,H)$=7.5 Hz, $^4J(H,H)$=1.3 Hz; ar-H); $^{13}$C NMR (75.5 MHz, $CDCl_3$, 20° C.) : δ=22.74 ($CH_3$), 69.73 (CHOH), 129.09, 129.31 (CH), 133.71 ($C_q$), 134.44 (CH), 202.82 (CO); GCMS: $R_t$=7.70 min; m/z (%)=150 (0.2) [$M^+$], 135 (1.3) [$M^+$—$CH_3$], 105 (100) [$C_7H_5O^+$], 77 (57) [$C_6H_5^+$], 51 (17) [$C_5H_3^+$]; HPLC: (Chiralpac AD, isohexane/isopropanol 90:10; 0.75 ml/min, 20° C., 21 bar) rt: 15.78 min.

(S)-Benzoin: $^1$H NMR (300 MHz, $CDCl_3$, 20° C., TMS): δ=4.56 (br, 1H; OH), 5.95 (s, 1H, CHOH), 7.5 (m, 6H, ar-H), 7.9 (m, 4H; ar-H); GCMS: $R_t$=11.29 min; m/z (%)=212 (0.5) [$M^+$], 105 (100) [$C_7H_5O^+$], 77 (40) [$C_6H_5^+$], 51 (9.8) [$C_4H_3^+$]; HPLC (Chiralpac AD, isohexane/isopropanol 90:10; 0.75 ml/min, 20° C., 21 bar) rt: 33.36 min.

Synthesizing (R)-2-HPP from Benzaldehyde 318 mg (3 mM) of benzaldehyde are dissolved in a mixture of 20 ml of DMSO and 100 ml of potassium phosphate buffer (50 mM, pH 7.0) containing 2.5 mM $MgSO_4$ and 0.15 mM TPP. The reaction is started by adding 1 mg (20 U) of benzaldehyde lyase and the mixture is incubated at room temperature. 88 mg (2 mM) of acetaldehyde are added to this reaction mixture. After a further 1 mg (20 U) of benzaldehyde lyase has been added, the reaction mixture continues to be incubated at room temperature. After 24 hours, a further 1 mg of benzaldehyde lyase and 88 mg of acetaldehyde are added. The course of the reaction is observed by means of a combination of gas chromatography and mass spectroscopy (GC-MS) or by means of high pressure liquid chromatography (HPLC). This procedure is repeated every 24 hours until the (R)-benzoin which is present has been completely reacted. HPLC analyses show that, after a total of 62 hours, it is only the product (R)-2-HPP which is present, with a 97% conversion having taken place. The reaction mixture is extracted with 250 ml of dichloromethane and the organic phase is washed with 25 ml of dist. water and 25 ml of a saturated solution of NaCl and dried over $Na_2SO_4$. The solvent is then removed in vacuo. The crude product is purified by means of column chromatograhy on silica gel ($CH_2Cl_2$) . This results in 214 mg (95%) of (R)-2-HPP, with the enantiomeric excess (ee) being >99% ($[\alpha]_D^{22}$=−122 (c=2, $CHCl_3$))

Legend to the Sequence Listing

The Sequence listing contains the nucleotide sequence encoding a *Pseudomonas fluorescens* benzaldehyde lyase (SEQ ID No. 1) and the amino acid sequence which is deduced from it, and also a separate depiction of the amino acid sequence (SEQ ID No. 2) of the *Pseudomonas fluorescens* benzaldehyde lyase.

What is claimed is:

1. An isolated benzaldehyde lyase, which has an amino acid sequence as depicted in SEQ ID No. 2.

2. A benzaldehyde lyase as claimed in claim 1, which has been isolated from microorganisms of the genus *Pseudomonas* or *Acinetobacter*.

3. A benzaldehyde lyase as claimed in claim 1, which has been isolated from the species *Pseudomonas fluorescens*.

* * * * *